United States Patent [19]  [11] 4,357,475
Hanotier et al.  [45] Nov. 2, 1982

[54] PROCESS FOR THE PRODUCTION AND THE RECOVERY OF TEREPHTHALIC ACID

[75] Inventors: Jacques D. Hanotier, Saint-Lambert; Jacques F. Dauby, Groot-Bijgaarden, both of Belgium

[73] Assignee: Labofina, S.A., Brussels, Belgium

[21] Appl. No.: 186,101

[22] Filed: Sep. 11, 1980

[30] Foreign Application Priority Data

Mar. 21, 1980 [GB] United Kingdom ............... 8009682

[51] Int. Cl.$^3$ .................... C07C 51/16; C07C 51/42
[52] U.S. Cl. ................................. 562/414; 562/412; 562/486
[58] Field of Search .............. 562/412, 416, 486, 414

[56] References Cited

U.S. PATENT DOCUMENTS 3,637,829  1/1972  Kerr ................................. 562/416
3,850,983  11/1974 Park ................................. 562/486
3,865,870  2/1975  Cronauer et al. ............... 562/412
4,268,690  5/1981  Komatsu et al. ................ 562/416

*Primary Examiner*—Alan Siegel

[57] ABSTRACT

The reaction mixture obtained by oxidizing p-xylene in the presence of water as diluent, at a temperature comprised between 140° and 220° C., and consisting of terephthalic acid crystals in suspension in an aqueous solution comprising unreacted p-xylene, intermediate oxidation products thereof, the heavy-metal catalyst and water is introduced in the upper part of a sedimentation column wherein the acid is separated by gravity and is washed with a counter current of water introduced near the bottom of said column, the temperature of the washing zone being higher than the minimum value $T_w$ given by the equation $T_w = 144 + 0.225\ T_R$, wherein $T_R$ is the oxidation temperature.

7 Claims, 1 Drawing Figure

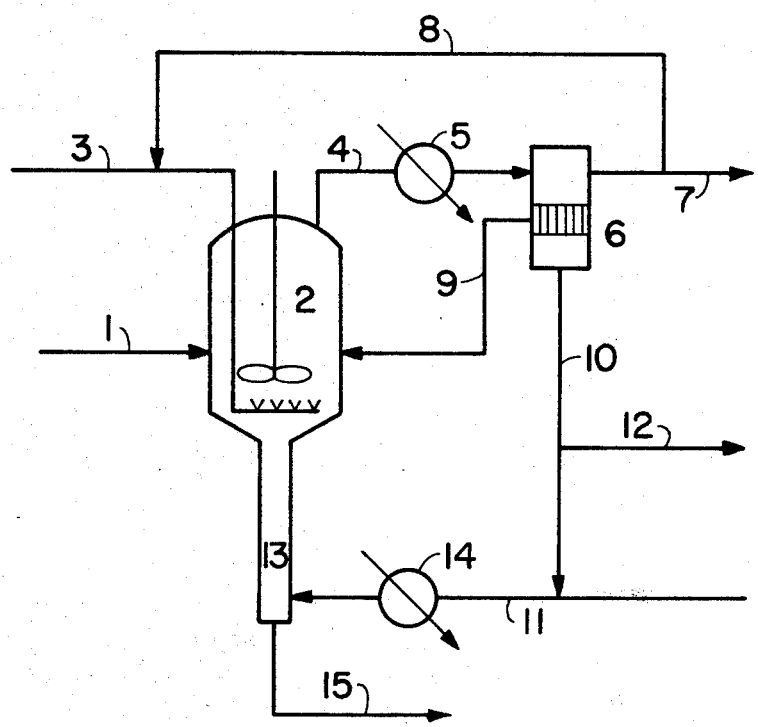

PROCESS FOR THE PRODUCTION AND THE RECOVERY OF TEREPHTHALIC ACID

This invention relates to a continuous process for the production of terephthalic acid by oxidation of p-xylene with a gas containing molecular oxygen in the presence of a heavy metal catalyst and of water in substantial amount as a diluent of the organic reaction mixture, and more particularly relates to a continuous process for the recovery of terephthalic acid from said reaction mixture.

The oxidation of p-xylene into terephthalic acid is a process of great commercial importance as terephthalic acid is used world-wide as a starting material for the manufacture of polyester fibers and films. According to the most practiced method, p-xylene dissolved in acetic acid is contacted with air at high temperature and pressure in the presence of a heavy metal catalyst and of an activator, generally a bromine-containing compound. Under these conditions, p-xylene is almost completely transformed into terephthalic acid which is withdrawn from the reaction zone as a slurry in the acetic medium. Crude terephthalic is then separated by a conventional solid-liquid separation device such as filtration or centrifugation and further purified while the filtrate comprising acetic acid, water of reaction and other light oxidation by-products is separately processed for recovering substantially anhydrous acetic acid for recycle.

Although this method has proven to be valid in practice and is used widely and successfully at the commercial scale, it suffers from having serious drawbacks so that research work is still being carried out world-wide to find out new methods and/or improvements for producing terephthalic acid at reduced costs. One of these drawbacks comes from the fact that acetic acid used as a solvent is burned in an amount which may be as high as 80 to 160 kg pe metric ton of terephthalic acid produced as disclosed in Belgian Pat. No. 857,068. Furthermore, the presence of bromine as a promoter in this method results in the fact that the reaction medium is highly corrosive which makes it necessary to use expensive construction materials such as titanium not only for the reactor itself but also for other major parts of the downstream equipment, e.g. heat exchanger, gas-liquid separator and other separation equipment such as centrifuges, etc.

To avoid those problems, other processes have been proposed wherein neither solvent nor bromine is used: p-xylene is oxidized by air in a reaction mixture which comprises in addition to the starting hydrocarbon nothing but terephthalic acid, intermediate oxidation products, i.e. mainly p-toluic acid, and minor amounts of water of reaction. However, in the absence of a diluent to maintain terephthalic acid as a fluid suspension and the intermediate oxidation products into solution, other problems are encountered which are related to handling the reaction mixture, separating terephthalic acid therefrom and to removing heat of reaction without extensive fouling of the heat exchangers.

More recently, the Applicant has proposed to carry out the oxidation of p-xylene in the absence of any promoter but in the presence of substantial amounts of water as a diluent. The advantages of using water for this purpose are obvious; briefly stated they are the following: (1) water is cheap, (2) it is definitely inert to oxidation, (3) it is especially efficient for absorbing the heat of reaction by vaporization, (4) it is easily separated from p-xylene by simple decantation, (5) it is not corrosive, (6) it is not pollutant, and (7) terephthalic acid separated from the reaction mixture is water-wet and can be directly used in any further purification procedure in water medium, e.g., by hydrogenation or post oxidation. However, water can act as a true diluent for the compounds to be oxidized, i.e. p-xylene in admixture with intermediate oxidation products, only when temperature is above a critical value generally comprised between 140° and 220° C. Depending upon the dilution chosen and the proportion of p-xylene in said compounds. Consequently to take advantage of the use of water as a diluent in handling the reaction mixture and separating terephthalic acid therefrom it is necessary to carry out these operations at relatively high temperatures and therefore under relatively high pressures, i.e. generally between 5 and 25 atmospheres, conditions which are generally outside the range of normal utilization of conventional equipment for solid-liquid separations such as filtration or centrifugation.

It is an object of the present invention to provide a process for the continuous production of terephthalic acid by oxidation of p-xylene in an aqueous medium. It is a more specific object of this invention to provide an improved method for the separation of terephthalic acid crystals from said medium. It is another object of this invention to provide such a method whereby this separation is accomplished efficiently and continuously at relatively high temperature and pressure in a simple equipment.

Accordingly, the present invention provides a process for the production of terephthalic acid by feeding continuously p-xylene into an oxidation zone where it is oxidized with an oxygen-containing gas at a temperature comprised between 140° and 220° C. in the presence of a heavy-metal catalyst and of water as a diluent, which comprises feeding the resulting reaction mixture consisting of terephthalic acid crystals in suspension in an aqueous solution comprising unreacted p-xylene, intermediate oxidation products thereof, the heavy-metal catalyst and a substantial amount of water into the upper part of a sedimentation column wherein terephthalic acid is separated by gravity from the other components of the reaction mixture and washed with a countercurrent of fresh water introduced near the bottom of said column, the temperature of the washing zone being maintained at a value higher than the minimum value $T_w$ given by the following equation:

$$T_w = 144 + 0.225 T_R \qquad (1)$$

$T_R$ being the temperature in degrees C. of the reaction mixture in the oxidation zone, and recovering crude terephthalic acid from the bottom of the sedimentation column as a slurry in water substantially free from intermediate oxidation products and heavy metal catalyst.

It is well known to carry out the removal of a soluble fraction from an insoluble solid phase without resorting to sophisticated and costly equipment by the method usually called leaching, lixiviation or decantation-settling. This operation can easily be carried out continuously generally in a column where the flow of solid proceeds downward, countercurrent to the flow of solution diluent. This technique is frequently applied to the recovery and washing of crystals formed in processes where a solid material has to be purified by recrystallization. With conventional solid-liquid separation devices, such as filtration or centrifugation, several successive separations and repulping in fresh solvent are generally needed for achieving efficient washing, operations which can be simultaneously and continuously carried out in a single countercurrent washing column. Such a column specially designed for the purification of crude dimethylterephthalate in methanol is described in U.S. Pat. No. 4,040,793: molten dimethylterephthalate is fed into the upper part of the column where it crystallizes immediately and settles countercurrent to a flow of methanol down to the bottom from which pure crystallized dimethylterephthalate is continuously discharged as a slurry in pure methanol; impurities-containing methanol is discharged through the solvent outlet at the upper part of the column. In a similar process for the purification of 4-methyl-2,6-di-t-butylphenol by crystallization in ethanol, the washing column is directly connected to a stirred crystallizer: crystals formed in the latter move downward into the former wherein they are washed by a countercurrent of fresh ethanol (Belgian Pat. No. 852,507).

In a process for the recovery and purification of terephthalic acid from the dipotassium salt thereof, two such washing columns connected in series are operated. In this case, water is used as washing solvent to remove potassium salts from terephthalic acid which is recovered as a slurry in water from the bottom of the second column (U.S. Pat. No. 3,873,612). More recently, processes have been described for the oxidation of p-xylene into terephthalic acid wherein the latter is continuously removed from the reaction mixture and washed in the same type of sedimentation columns as in the aforementioned purification procedures. In these processes, washing of the terephthalic acid crystals is carried out with the same solvent as used in the oxidation zone to dilute the compounds being oxidized, i.e. preferably acetic acid. In this way, the washing column can be fed with the liquid material stripped as vapors from the oxidation zone by the effluent gas, eventually after removal by distillation of the water of reaction contained therein (U.K. patent application Nos. 2,000,493 and 2,014,985).

From the foregoing, it will be apparent that the most appropriate method for the recovery of terephthalic acid produced by air oxidation of p-xylene and/or oxidation intermediates thereof such as p-toluic acid in aqueous medium at relatively high temperature and pressure is through settling countercurrent to a stream of water in a sedimentation column. However, in experiencing this method troubles are frequently encountered as made apparent from the fact that less terephthalic acid than actually produced by oxidation of the p-xylene fed into the reaction zone is recovered from the bottom of the column with the consequence that accumulation of terephthalic acid takes place in the oxidation reactor. Moreover, in these cases, terephthalic acid recovered from the bottom of the column is generally contaminated by substantial amounts of water-soluble components of the reaction mixture, that is countercurrent washing of the terephthalic acid crystals in the column does not take place efficiently.

Although any definite explanation of these undesired phenomena cannot be given heretofore, it is believed that they are associated with phase separation taking place in the sedimentation column as dissolved organic materials become more diluted by the ascending stream of fresh water. Whatever the exact physical mechanism of these undesired phenomena can be, we have found that they can be avoided by carefully adjusting the operating temperature in the sedimentation column, or at least in the part thereof where separation takes place between terephthalic acid and the water-soluble components of the reaction mixture.

In accordance with the present invention, the operating temperature in the sedimentation column should be higher than a critical temperature $T_w$ which depends on the temperature $T_R$ of the reaction mixture in the oxidation zone according to equation (1) given hereabove. The temperature in the sedimentation column will be comprised between this minimum value $T_w$ and about 240° C. At operating temperatures in said column higher than about 240° C., exceedingly large amounts of crystals of terephthalic acid would be dissolved in water. Below this critical temperature $T_w$, the undesired phenomena referred to hereabove are likely to take place therefore hindering separation and efficient washing of terephthalic acid. From equation (1), it can be inferred that when $T_R$ is lower than about 186° C., the temperature in the sedimentation column must be significantly higher than $T_R$ in order to prevent those undesired phenomena from taking place. On the other hand, when $T_R$ is higher than about 186° C., the temperature in the sedimentation column may be higher, equal or even lower than $T_R$. In this case, a lower temperature, i.e. comprised between $T_R$ and $T_w$ as given by equation (1) will be preferred so as to prevent as much as possible backmixing in the column; moreover, a lower temperature will help to reduce corrosion in said column, therefore allowing the use of conventional materials for the construction thereof. But in any case, the temperature in the column must be higher than the minimum value $T_w$ as given by equation (1).

In operating this process, it is especially advantageous to use water stripped as vapours from the oxidation reactor as washing solvent for terephthalic acid in the sedimentation column. For that, nothing but condensing said vapours and separating supernatant p-xylene by decantation is required; the hydrocarbon phase can be directly recycled into the oxidation reactor and the aqueous phase injected into the bottom of the sedimentation column. The water solution recovered from the top of the column and containing the water-soluble components of the oxidation reaction mixture together with small particles of solid material can be directly introduced, without any treatment, into the oxidation reactor. For this purpose, it is advantageous to have the washing column directly connected to the bottom of the oxidation reactor; the upward stream of water then enters directly the oxidation reactor without requiring any conveying system such as a pump. The assembly thus realized constitutes a physico-chemical system wherein nothing but p-xylene and air is introduced and from which only the ultimate products of the reaction, namely terephthalic acid, carbon oxides and water are withdrawn. This is certainly an advantageous system from the standpoints of simplicity of operation and of energy conservation.

However, it is to be realized that by proceeding in this way, some light degradation by-products such as acetic acid and formic acid present in the condensed vapours may accumulate in the system. To avoid such an accumulation, some purge may be necessary; this can be achieved for instance by discarding a part of the condensed aqueous phase but this part can be relatively small as formic acid as well as acetic acid can be tolerated in substantial amounts in the oxidation reaction mixture. It is indeed a surprising feature of the present process that formic acid which is known as being a powerful inhibitor for most catalytic oxidations, either in the absence of a solvent or in the presence of such organic solvents as acetic acid, is little detrimental in the aqueous system of the present invention even when present in amounts as high as 10% by weight or even more. Similarly, such strong polycarboxylic acids as trimellitic acid which are always formed as heavy by-products when p-xylene is oxidized into terephthalic acid and which are known as being highly noxious in most processes of the prior art are relatively inocuous in the aqueous system of the present process. Moreover, and this is another surprising feature of this invention, those polycarboxylic acids as well as formic acid undergo extensive degradation reactions with the consequence that they are ultimately removed from the reaction medium in the form of carbon oxides. Under such circumstances, building up of these by-products does not take place beyond relatively low levels so that special purging systems for the removal thereof are generally not necessary.

In practice, the process of the present invention can be carried out as depicted schematically on the accompanying drawing. On the drawing, the sedimentation column 13 is shown directly connected to the bottom of the oxidation reactor 2 but, obviously, both can also be operated as separate vessels. The latter assembly may be more advantageous when some purge is necessary but, as already pointed out, a conveying system such as a pump has then to be provided for recycling into the reactor the mother liquors and washing solvent from the upper part of the column. Referring to the drawing, fresh p-xylene is introduced through line 1 into oxidation zone 2 where it is reacted with air from line 3 and transformed into different intermediate oxidation compounds, i.e. predominently p-toluic acid, and ultimately into terephthalic acid. Oxygen-depleted air leaves the oxidation zone through line 4 together with vapours consisting of water, p-xylene and minor amounts of light by-products, namely acetic acid and formic acid. These vapours are condensed in condenser 5 and separated from the exhaust gas in gas-liquid separator 6. The exhaust gas leaves the system through line 7; however a part thereof is recycled via line 8 into the oxidation zone so as to ensure therein adequate temperature control through vaporization of the volatile components of the reaction mixture, i.e. substantially water and p-xylene, and also to provide enough water solvent to wash terephthalic acid as explained below. In separator 6, the liquid condensate separates into two distinct phases: an upper organic phase consisting predominantly of p-xylene which is recycled through line 9 into the oxidation zone and a lower aqueous phase which is withdrawn through line 10 and mixed in line 11 with fresh water for being used as washing solvent for terephthalic acid. Some part of this aqueous phase from separator 6 may be discarded through line 12 as a purge. When the controls of terephthalic acid formed in the oxidation zone have grown up to a sufficient size, they fall down into washing zone 13 wherein they are leached with ascending washing solvent i.e. substantially water, introduced near the bottom of the washing zone through line 11 via heater 14 where said washing solvent is brought to the appropriate temperature in accordance with formula (1) given hereinbefore. To ensure uniform temperature in the washing zone and efficient contact between crystals and the ascending flow of solvent, a packing, static mixer or any known appropriate distributing system can be used with advantage. Terephthalic acid substantially free from adhering water-soluble impurities is then withdrawn through line 15 from the bottom of the washing zone as a slurry in washing solvent.

The slurry of terephthalic acid thus recovered from the washing zone can be further heated up to such an elevated temperature as to achieve complete solubilization for further processing, e.g. purification up to the fiber grade by hydrogenation or any other purification procedure. Alternately, this slurry can be discharged onto a filter or a centrifuge to separate crude terephthalic acid as a solid. In the latter case, it is preferred that the slurry be cooled down to a relatively low temperature, i.e. below 100° C. so as to allow the solid-liquid separation to be carried out under atmospheric pressure. This cooling can be carried out in a separate vessel but another possibility is to bring the lower part of the washing column at said relatively low temperature by any known means such as a cooling jacket.

As those skilled in the art will appreciate, many other modifications can be brought to the above procedure without departing from the scope of the present invention which will now be further described by means of the following examples.

EXAMPLE 1 p-Xylene was oxidized in flow in the same type of apparatus as shown in the accompanying drawing except that the aqueous condensate from separator 6 was completely discarded through line 12 and that only fresh water was used in line 11 to feed washing zone 13. Another difference was that temperature control in the oxidation zone was not achieved by recycling therein a part of the exhaust gas but by carefully adjusting the temperature of the oil circulated in the heating jacket. All metal parts of equipment were in 316 stainless steel.

The temperature in the oxidation zone ($T_R$) and in the washing zone ($T_w$) was 190° C. and the pressure was 20 kg/cm$^2$. To start the operation, a mixture of p-xylene, p-toluic acid, water and metal catalyst was charged into the oxidation zone and heating was applied while stirring and admitting air at a rate of about 400 liters (measured at room temperature and atmospheric pressure) per kg of reaction mixture. The reaction was first carried out batchwise for sometime; then p-xylene was fed continuously into the oxidation zone and terephthalic acid produced in the reaction was withdrawn as a slurry in water from the bottom of the washing zone. After about 14 hours of continuous operation a steady state was attained in the different parts of the system as attested by the fact that the composition of the various effluent streams was substantially stabilized. Nevertheless, the operation was still continued for further 16 hours. The reaction mixture in the oxidation zone and the various effluent streams were then thoroughly analyzed. The results thus obtained are shown in Table 1 for 1000 parts by weight of reaction mixture.

Individual samples of crude terephthalic acid recovered from line 15 were filtered, dried and analyzed separately. A typical composition is given herebelow, in weight %.

Terephthalic acid: 92.68%
p-Toluic acid: 4.93%
4-Carboxybenzaldehyde: 2.24%
Heavy by-products: 0.12%
DMF Color (Hazen number): 12 apha
Cobalt (ppm): <1

Manganese (ppm): <1

EXAMPLE 2

The same operation as in the preceding example was carried out with the difference that the temperature in the oxidation zone and in the washing zone was 185° C. instead of 190° C. and that the rate of p-xylene feeding was 38 parts per hour instead of 30 parts for 1000 parts by weight of reaction mixture.

acid recovered under these conditions from the bottom of the washing zone was the following, in weight %:
*for 1000 parts by weight of reaction mixture.
Terephthalic acid: 94.80%
p-Toluic acid: 3.09%
4-Carboxybenzaldehyde: 2.09%
Heavy by-products: undetected
DMF color (Hazen number): 10 apha.

By comparing this composition with the one given in

TABLE 1

| Components | In the oxidation zone (parts by weight) | In lines (parts per hour) | | | | |
|---|---|---|---|---|---|---|
| | | 1 | 7 | 10 | 11 | 15 |
| p-Xylene | 40.65 | 29.95 | 2.55 | | | |
| p-Toluic acid | 233.47 | | | | | 2.08[(2)] |
| 4-Carboxybenzaldehyde | 17.07 | | | | | 0.81 |
| Other intermediates | 11.47 | | | | | |
| Terephthalic acid | 100.54 | | | | | 33.03 |
| Heavy by-products | 29.79 | | | | | 0.05 |
| Light acids (acetic, formic) | 7.93 | | <0.01 | 1.16 | | |
| Carbon oxides | | | 9.33 | | | |
| Water | 558.30 | | | 150.92 | 664.74 | 513.82 |
| Catalysts (cobalt and manganese)[(1)] | 0.78 | | | | | <6 ppm |
| Total | 1000.00 | | | | | |

[(1)]Concentration of catalysts in mmoles per kg of liquid reaction mixture: manganese, 7.5; cobalt, 7.8
[(2)]Including 0.18 parts of p-toluic acid dissolved in water.

After about 30 hours of continuous operation, the crystals recovered from line 15 were yellow and the analysis of a typical sample showed these crystals to be only 75.8% by weight in terephthalic acid; p-toluic acid amounted to 20.4% showing that the product as heavily contaminated by the reaction mixture from the oxidation zone.

Temperature was then raised up to 190° C. Immediately, the crystals recovered from line 15 turned white and, upon analysis of a typical sample, were shown to be 92.9% by weight in terephthalic acid, which is substantially identical to the value determined for the product obtained in the previous example.

The reaction was still continued at 190° C. for 8 hours and the resulting reaction mixture was thoroughly analyzed as in the preceding example. The composition thus described was the following in % by weight:
p-Xylene: 5.7%
p-Toluic acid: 28.6%
4-Carboxybenzaldehyde: 2.3%
Other intermediates: 1.4%
Terephthalic acid: 18.2%
Heavy by-products: 1.9%
Water: 41.9%

By comparing these values with those given in the preceding example for the composition of the reaction mixture at the steady state, it can be shown that increasing the feeding rate of p-xylene in the oxidation zone resulted in increasing substantially the content of organic materials in the system at the expense of water diluent.

EXAMPLE 3

The same operation in Example 1 was carried out except that the air flow rate into the oxidation zone was so adjusted that the aqueous phase withdrawn from the system through line 10 amounted to 166 parts instead of 152 parts. As a result, the ascending stream of solvent in the washing zone was correspondingly increased. The composition of a typical sample of crude terephthalic Example 1 for a typical sample of crude terephthalic acid, it can be seen that a substantial improvement in the quality of the product has resulted from only slightly increasing the ascending rate of washing solvent. This illustrates the importance of the washing conditions which can be easily selected by the skilled worker in consideration of the characteristics of the particular sedimentation column used, i.e. length, diameter, packing.

EXAMPLE 4

This example illustrates that in oxidations taking place in a reaction medium comprising mainly p-toluic acid and water, the presence of substantial amounts of trimellitic acid which might accumulate as a by-product in the process of the present invention has in fact little influence upon the reaction rate.

Into an autoclave of one-liter capacity equipped with a mechanical agitation device, a heating jacket, a gas inlet tube and a vent there was charged:
p-Toluic acid: 125 g
Water: 125 g
Manganese acetate: 2.50 millimoles
Cobalt acetate: 2.50 millimoles The reactor was then pressurized with air up to a pressure of 20 kg/cm$^2$ and the above mixture was heated for two hours at 185° C. while stirring and admitting air at a flow rate of 90 liters per hour.

In another experiment, the same procedure was repeated except that 12.5 g of trimellitic acid was added to the charge, i.e. about 10% by weight of the amount of p-toluic acid contained therein. For both experiments the absorption of oxygen and the evolution of carbon dioxide were followed and determined. The results thus obtained are shown in Table 2. They show that oxygen absorption was relatively little affected by the presence of trimellitic acid in the reaction medium. By contrast, about twice as much carbon dioxide was evolved which may be ascribed to degradation of trimellitic acid through decarboxylation Substantially, the same results were obtained when some p-xylene was present as substrate in the charge in addition to p-toluic acid.

TABLE 2

| Trimellitic acid in the charge | $O_2$ absorbed moles | $CO_2$ evolved moles | Combustion ratio $CO_2/O_2$ |
|---|---|---|---|
| No | 0.596 | 0.054 | 0.09 |
| Yes | 0.545 | 0.098 | 0.18 |

We claim:

1. A process for the production and the recovery of terephthalic acid which comprises the steps of:

feeding continuously a bromine-free, substantially liquid aqueous mixture consisting of p-xylene, p-toluic acid and a solvent consisting essentially of water into an oxidation reactor where it is oxidized with an oxygen-containing gas at a temperature of from 140° C. to 220° C. in the presence of a heavy-metal catalyst, feeding the resultant reaction mixture consisting of terephthalic acid crystals in suspension in an aqueous solution comprising unreacted p-xylene, intermediate oxidation products thereof, the heavy-metal catalyst and water in the upper part of a sedimentation column wherein terephthalic acid crystals are separated by gravity from the other components of the reaction mixture and are washed with a countercurrent of water introduced near the bottom of said column, the temperature in the sedimentation column being maintained at a value higher than the minimum value $T_W$ given by the equation $T_W = 144 + 0.225 T_R$, wherein $T_r$ is the temperature of the reaction mixture in the oxidation reactor, and not higher than 240° C., and recovering crude terephthalic acid from the bottom of the sedimentation column as a slurry in water substantially free from intermediate oxidation products and heavy metal catalyst.

2. Process as claimed in claim 1, wherein the temperature of said washing zone is maintained between a value higher than said minimum value $T_W$ and 240° C.

3. Process as claimed in claim 1, wherein the vapours from the oxidation reactor are condensed and the resulting aqueous phase is introduced near the bottom of said sedimentation column.

4. Process as claimed in claim 1, wherein the water solution recovered from the top of the sedimentation column and containing the water-soluble components of the oxidation reaction mixture together with small particles of solid material is directly recycled into said oxidation reactor.

5. Process as claimed in claim 4, wherein said water solution recovered from the top of the sedimentation column enters directly the oxidation reactor, the bottom of said oxidation reactor being directly connected to the top of the sedimentation column.

6. Process as claimed in claim 1, wherein the oxygen-depleted gas and the vapors leaving the oxidation reactor pass through a condenser where the liquid condensate separates into an upper organic phase and a lower aqueous phase, a part of the gas is recycled into the oxidation reactor, the organic phase is recycled into the oxidation reactor and the aqueous phase is mixed with fresh water, the mixture being introduced near the bottom of the sedimentation column.

7. A process for the production and recovery of terephthalic acid which comprises the steps of:

feeding continuously a bromine-free, substantially liquid aqueous mixture consisting essentially of p-xylene, p-toluic acid and a solvent consisting essentially of water into an oxidation reactor where it is oxidized with an oxygen-containing gas at a temperature of from 140° C. to 220° C. in the presence of a heavy metal catalyst to produce a reaction mixture consisting of terephthalic acid crystals in suspension in an aqueous solution comprising unreacted p-xylene, intermediate oxidation products thereof, the heavy-metal catalyst and water, with formation of oxygen-depleted gas and vapours leaving the oxidation reactor, feeding continuously said reaction mixture into the upper part of a sedimentation column wherein terephthalic acid crystals are separated by gravity from the other components of the reaction mixture and are washed with a countercurrent of water introduced near the bottom of said column, the temperature in the sedimentation column being maintained at a value higher than the minimum value $T_W$ given by the equation $T_W = 144 + 0.225 T_R$, wherein $T_R$ is the temperature of the reaction mixture in the oxidation reactor, and not higher than 240° C., passing continuously the oxygen-depleted gas and the vapours leaving the oxidation reactor through a condenser wherein a liquid condensate separates into an upper organic phase and a lower aqueous phase, recycling a part of the gas into the oxidation reactor, recycling the organic phase into the oxidation reactor, mixing the aqueous phase with fresh water and using said mixture as the countercurrent of water introduced near the bottom of the sedimentation column, recovering crude terephthalic acid from the bottom of the sedimentation column as a slurry in water, recovering continuously from the top of the sedimentation column an aqueous solution containing the water-soluble components of the oxidation reaction mixture together with small particles of solid material and recycling directly said aqueous solution into the oxidation reactor.

* * * * *

UNITED STATES PATENT AND TRADEMARK OFFICE
CERTIFICATE OF CORRECTION

PATENT NO. : 4,357,475
DATED : November 2, 1982
INVENTOR(S) : Jacques D.V. Hanotier, Jacques F. Dauby It is certified that error appears in the above—identified patent and that said Letters Patent is hereby corrected as shown below:

In Column 5, Line 58, delete "controls" and substitute therefor --crystals--.
In Column 6, Line 46, delete "sometime" and substitute therefor --some time--.
In Column 7, Line 33, delete "as" and substitute therefor --was--; and in Column 7, Line 62, after "operation" add --as--.
In Column 8, Line 3, after "parts" add --*--.
In Column 9, Line 33, delete "$T_W$" and substitute therefor --$T_w$--; Column 9, Line 34, after "equation" delete "$T_W$" and substitute therefor --$T_w$--; Column 9, Line 34, after "wherein" delete "$T_r$" and substitute therefor --$T_R$--; and in Column 9, Line 43 delete "$T_W$" and substitute therefor --$T_w$--.
In Column 10, Line 35, after "value" delete "$T_W$" and substitute therefor --$T_w$--; and in Column 10, Line 35 after "equation" delete "$T_W$" and substitute therefor --$T_w$--.

Signed and Sealed this

Third Day of May 1983

[SEAL]

Attest:

GERALD J. MOSSINGHOFF

Attesting Officer   Commissioner of Patents and Trademarks